US010639065B2

(12) United States Patent
Onuma

(10) Patent No.: US 10,639,065 B2
(45) Date of Patent: May 5, 2020

(54) MEDICAL ASSIST DEVICE

(71) Applicant: Canon U.S.A., Inc., Melville, NY (US)

(72) Inventor: Kazufumi Onuma, Irvine, CA (US)

(73) Assignee: Canon U.S.A., Inc., Melville, NY (US)

( * ) Notice: Subject to any disclaimer, the term of this patent is extended or adjusted under 35 U.S.C. 154(b) by 261 days.

(21) Appl. No.: 14/804,824

(22) Filed: Jul. 21, 2015

(65) Prior Publication Data

US 2017/0020557 A1 Jan. 26, 2017

(51) Int. Cl.
A61B 17/34 (2006.01)
A61B 17/00 (2006.01)
A61B 90/00 (2016.01)

(52) U.S. Cl.
CPC ........ *A61B 17/3403* (2013.01); *A61B 2017/00075* (2013.01); *A61B 2017/3407* (2013.01); *A61B 2017/3409* (2013.01); *A61B 2090/0808* (2016.02)

(58) Field of Classification Search
CPC ........ A61B 17/3403; A61B 2090/0808; A61B 2017/00075; A61B 2017/3407; A61B 2017/3409; A61B 34/20; A61B 34/25; A61B 2034/2059
USPC ........................................... 606/130
See application file for complete search history.

(56) References Cited

U.S. PATENT DOCUMENTS

| 4,841,967 A | 6/1989 | Chang et al. |
| 5,196,019 A | 3/1993 | Davis et al. |
| 5,201,742 A | 4/1993 | Hasson |
| 5,280,427 A | 1/1994 | Magnusson et al. |
| 5,682,892 A | 11/1997 | Selder et al. |
| 5,957,934 A | 9/1999 | Rapoport |
| 6,079,681 A | 6/2000 | Stern et al. |
| 6,119,032 A | 9/2000 | Martin et al. |
| 6,185,445 B1 | 2/2001 | Knuttel |
| 6,676,669 B2 | 1/2004 | Charles et al. |
| 7,083,608 B2 | 8/2006 | Tomita et al. |
| 7,187,104 B2 | 3/2007 | Yamamoto et al. |
| 7,379,769 B2 | 5/2008 | Piron et al. |
| 7,636,596 B2 | 12/2009 | Solar |
| 7,824,417 B2 | 11/2010 | Magnusson et al. |

(Continued)

FOREIGN PATENT DOCUMENTS

| CA | 2784988 A | 2/2013 |
| EP | 2561821 A1 | 2/2013 |

(Continued)

OTHER PUBLICATIONS

Fischer, G. S.,et al., "MRI Guided Needle Insertion—Comparison of Four Technique", In Annual Scientific Conference of the Society of Interventional Radiology 31, 2006. (Abstract only).

(Continued)

*Primary Examiner* — Richard G Louis
(74) *Attorney, Agent, or Firm* — Canon U.S.A., Inc., IP Division

(57) ABSTRACT

A medical assistance device is provided for insertion of a needle-like instrument. The device comprises a guide unit, a mechanism including the guide unit, a driving source configured to drive the mechanism, a needle sensor; and an anti-driving unit. The medical assistance device can detect the insertion state of a needle-like device and, when required, the anti-driving unit prevents operation of the driving source.

22 Claims, 6 Drawing Sheets

(56) References Cited

U.S. PATENT DOCUMENTS

| | | | |
|---|---|---|---|
| 8,241,301 B2 | 8/2012 | Zhang et al. | |
| 8,308,740 B2 | 11/2012 | Tolley et al. | |
| 2001/0000940 A1 | 5/2001 | Maruyama | |
| 2002/0019641 A1 | 2/2002 | Truwit | |
| 2002/0082612 A1* | 6/2002 | Moll | A61B 34/30 606/130 |
| 2003/0078502 A1* | 4/2003 | Miyaki | A61B 8/0833 600/461 |
| 2003/0107299 A1 | 6/2003 | Fujimoto | |
| 2004/0064148 A1 | 4/2004 | Daum et al. | |
| 2005/0261581 A1 | 11/2005 | Hughes et al. | |
| 2006/0149147 A1 | 7/2006 | Yanof | |
| 2006/0229641 A1 | 10/2006 | Gupta et al. | |
| 2007/0276407 A1 | 11/2007 | Vogele | |
| 2008/0004481 A1 | 1/2008 | Bax | |
| 2008/0009743 A1* | 1/2008 | Hayasaka | A61B 8/0833 600/461 |
| 2008/0033356 A1* | 2/2008 | Kluge | A61B 5/0531 604/117 |
| 2008/0161829 A1 | 7/2008 | Kang | |
| 2008/0167663 A1 | 7/2008 | De Mathelin | |
| 2009/0018390 A1* | 1/2009 | Honda | A61B 1/00059 600/106 |
| 2009/0079431 A1 | 3/2009 | Piferi et al. | |
| 2009/0234369 A1 | 9/2009 | Bax et al. | |
| 2010/0010505 A1 | 1/2010 | Herlihy et al. | |
| 2010/0082040 A1 | 4/2010 | Sahni | |
| 2010/0168766 A1* | 7/2010 | Zeng | A61B 17/3403 606/130 |
| 2011/0082468 A1* | 4/2011 | Hagag | A61B 34/20 606/130 |
| 2011/0190787 A1 | 8/2011 | Sahni | |
| 2011/0251624 A1 | 10/2011 | Yl | |
| 2012/0022368 A1 | 1/2012 | Brabrand et al. | |
| 2012/0143048 A1* | 6/2012 | Finlay | A61B 17/3403 600/424 |
| 2013/0069651 A1 | 3/2013 | Luminani | |
| 2013/0345718 A1 | 12/2013 | Crawford | |
| 2014/0052154 A1 | 2/2014 | Griffiths et al. | |
| 2014/0066944 A1* | 3/2014 | Taylor | B25J 15/0466 606/103 |
| 2014/0121675 A1 | 5/2014 | Bax | |
| 2014/0128881 A1 | 5/2014 | Tyc | |
| 2014/0128883 A1 | 5/2014 | Piron et al. | |
| 2014/0200445 A1 | 7/2014 | Boezaart et al. | |
| 2014/0275978 A1 | 9/2014 | Fujimoto et al. | |
| 2014/0275979 A1* | 9/2014 | Fujimoto | G01R 33/286 600/422 |
| 2014/0336670 A1 | 11/2014 | Brabrand et al. | |
| 2014/0350572 A1 | 11/2014 | Elhawary et al. | |
| 2015/0238266 A1 | 8/2015 | Fujimoto et al. | |
| 2016/0074063 A1 | 3/2016 | Arimitsu et al. | |
| 2017/0014200 A1 | 1/2017 | Onuma et al. | |
| 2017/0071626 A1 | 3/2017 | Onuma et al. | |
| 2017/0258489 A1* | 9/2017 | Galili | A61B 17/3403 |

FOREIGN PATENT DOCUMENTS

| | | |
|---|---|---|
| JP | 5-083961 A | 4/1993 |
| JP | 8-237971 A | 9/1996 |
| JP | 2004-320846 A | 11/2004 |
| JP | 2004320846 A | 11/2004 |
| WO | 2012178109 A1 | 12/2012 |
| WO | 2014152685 A1 | 9/2014 |
| WO | 2017/132505 A1 | 8/2017 |

OTHER PUBLICATIONS

Koethe, Y. et al., "Accuracy and efficacy of percutaneous biopsy and ablation using robotic assistance under computed tomography guidance: a phantom study", European Society of Radiology, 2013.

Maxio Brochure: Planning and Targeting for CT guided Procedures by Perfint.

Palmer, K., et al., "Development and evaluation of optical needle depth sensor for percutaneous diagnosis and therapies", Medical Imaging 2014: Image-Guided Procedures, Robotic Interventions, and Modeling, 2014, Proc. of SPIE vol. 9036, 90362M.

Song, S., et al., "Biopsy Needle Artifact Localization in MRI-guided Robotic Transrectal Prostate Intervention," IEEE Transactions on Biomedical Engineering, Jul. 2012, vol. 57, No. 7.

Song, S.E., et al., "Design Evaluation of a Double Ring RCM Mechanism for Robotic Needle Guidance in MRI-guided Liver Interventions", International Conference on Intelligent Robots and Systems, Nov. 3-7, 2013, pp. 4078-4083, Tokyo, Japan.

Hata, N. et al.,"MRI-Compatible Manipulator With Remote-Center-of-Motion Control", J. Magn. Reson Imaging, May 2008, vol. 27, vol. 5.

Perfint, Inc Maxio Robot—Features http://www.perfinthealthcare.com/MaxioFeatures.asp Accessed Sep. 11, 2015.

Palmer, K., et al., "Development and evaluation of optical needle depth sensor for percutaneous diagnosis and therapies", Medical Imaging 2014: Image-Guided Procedures, Robotic Interventions, and Modeling, 2014, accessed Jan. 14, 2015.

* cited by examiner

MEDICAL ASSIST DEVICE

BACKGROUND OF THE INVENTION

Field of the Invention

The present invention relates to a medical assist device that assists biopsy or treatment by puncture with a needle-like instrument.

Description of the Related Art

Needs of minimally invasive treatment are increasing to improve the quality of life (QOL) of patients in medical care. Percutaneous therapies, such as percutaneous ablation therapy and percutaneous cryotherapy, have been developed as minimally invasive treatments.

In such a percutaneous therapy, puncture has to be performed based on medical images captured by an imaging such as magnetic resonance imaging (MRI) or computed tomography (CT) because the target site is not directly seen. These images are not captured in a real-time manner because such a medical imaging apparatus is used. A special MRI apparatus enables real-time image capture. In this case, an operation has to be performed in a narrow space. It is difficult to accurately reach a target in either of the above-described cases. This results in time-consuming operation.

Under the above-described circumstances, a puncture assist device as described in U.S. Patent Application Publication No. 2006/0229641 has been developed as an operation assist using medical images, such as MRI or CT images. As described in U.S. Patent Application Publication No. 2006/0229641, the device disposed on a patient's abdomen adjusts an insertion trajectory relative to the position of a puncture target site specified using medical images to puncture the target side. This device is positioned in any orientation and any angle by motors, and accordingly readily assists puncture in a correct direction. In addition, a holder for an instrument can be moved to an open position to achieve safety after puncture. Consequently, if organs shift due to breathing or the like of a patient, the organs will be protected from excess stress because the instrument is free.

A device including a ring-shaped vibration-type actuator as described in U.S. Patent Application Publication No. 2014/0275979 has been developed for use in combination with an MRI apparatus. In addition to the ring-shaped vibration-type actuator, other actuators have been developed. For example, U.S. Pat. No. 7,187,104, herein incorporated by reference in its entirety (see also Japanese Patent Laid-Open No. 2004-320846) describes a plate-shaped vibration-type actuator utilizing displacement in its thickness direction. Japanese Patent Laid-Open No. 8-237971 describes a plate-shaped vibration-type actuator utilizing displacement in its longitudinal direction. Japanese Patent Laid-Open No. 5-083961 describes a composite actuator that achieves longitudinal vibration and torsional vibration using individual piezoelectric elements.

Assuming that the instrument is released, if an operation error or malfunction of the device occurs while the instrument is partly placed in a patient's body, the holder may be moved beyond the open position. In such a case, the holder may apply a large external force to the instrument partly placed in the patient's body. Unfortunately, the device may suffer from excess stress.

SUMMARY OF THE INVENTION

According to the present invention, while an instrument is inserted into or partly placed in a patient's body, an anti-driving unit is actuated to restrict automatic driving of a medical assist device. This prevents excess stress from being generated between the instrument and the device caused by an operation error or malfunction.

Further features of the present invention will become apparent from the following description of exemplary embodiments with reference to the attached drawings.

BRIEF DESCRIPTION OF THE DRAWINGS

FIGS. 5(a) and 5(b) illustrate a detachable guide unit in accordance with a modification of the first embodiment.

DESCRIPTION OF THE EMBODIMENTS

First Embodiment

Figure 1:
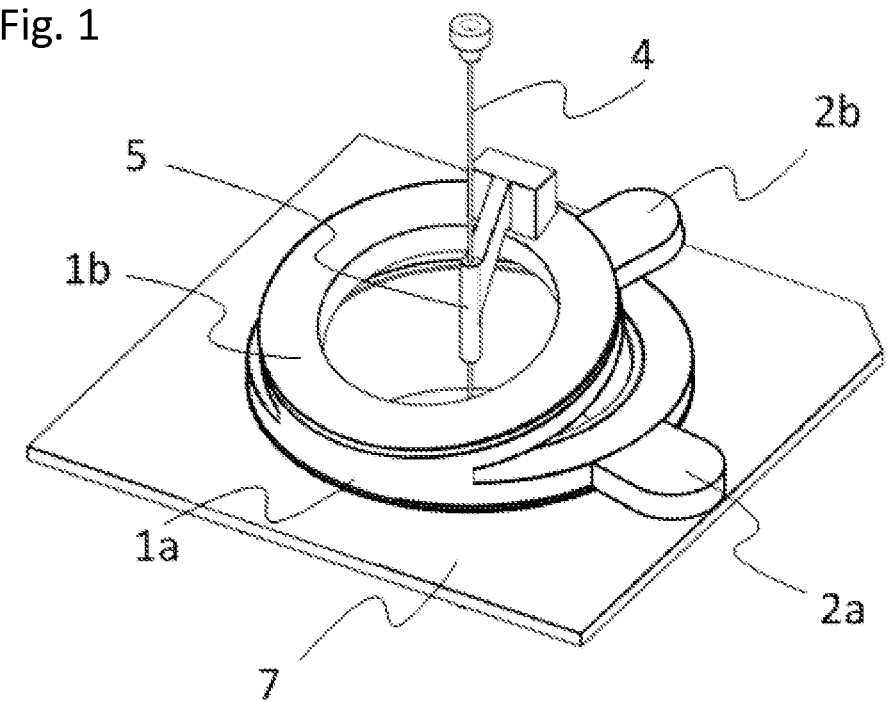
FIG. 1 illustrates an exemplary configuration of a mechanism in a first embodiment.

A first embodiment will be described with reference to FIGS. 1 to 7. A needle-like instrument guiding mechanism of a medical assist device according to the first embodiment and changing an insertion trajectory of a needle-like instrument will be described with reference to FIG. 1. An exemplary configuration and operation of a needle sensor for detecting attachment of the needle-like instrument and those of an anti-driving unit will then be described.

Insertion Guidance

The mechanism for guiding the needle-like instrument to the insertion trajectory will now be described. The medical assist device according to the first embodiment includes a base 7 to be disposed on a puncture target. The base 7 is provided with a ring-shaped first rotary member 1a disposed thereon. The first rotary member 1a is rotatable about a rotation axis perpendicular to the base 7. A first driving source 2a is interposed between the base 7 and the first rotary member 1a. The first rotary member 1a is driven relative to the base 7 by the first driving source 2a.

The first rotary member 1a is provided with a ring-shaped second rotary member 1b. The second rotary member 1b has a rotation axis at a predetermined angle to the rotation axis of the first rotary member 1a. Although such inclination is not particularly limited, it is assumed that an angle of inclination is 15 degrees in the present embodiment. A second driving source 2b is interposed between the first rotary member 1a and the second driving source 2b. The second rotary member 1b is driven relative to the first rotary member 1a by the second driving source 2b.

A first position sensor 3a for detecting a change in rotational position of the first rotary member 1a relative to the base 7 is disposed between the base 7 and the first rotary member 1a.

Similarly, a second position sensor 3b for detecting a change in rotational position of the second rotary member 1b relative to the first rotary member 1a is disposed between the first rotary member 1a and the second rotary member 1b. An example of each position sensor may be an optical encoder that includes a scale 32 including a ring-shaped reflector and a radially extending non-reflective grating pattern and an optical element 31 reading the grating pattern of the scale 32. Any other position sensor can be used.

Figure 2:
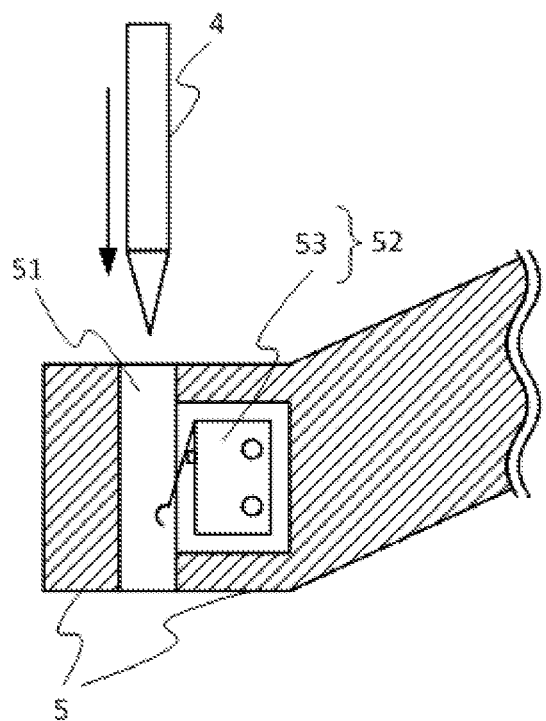
FIG. 2 illustrates an exemplary configuration of a needle sensor in the first embodiment.

The second rotary member 1b is provided with a guide unit 5 for defining the insertion trajectory of a needle-like instrument 4. In this embodiment, the guide unit 5 includes a hole-shaped needle attachment portion 51 as illustrated in FIG. 2. The insertion trajectory is defined by passing the needle-like instrument 4 through such a hole. The needle attachment portion 51 is not limited to the hole. The needle attachment portion 51 may be a groove as will be described later. The guide unit 5 or the needle attachment portion 51 is provided with a needle sensor 52, which will be described later, capable of detecting attachment of the needle-like instrument 4.

Rotating the second rotary member 1b allows inclination of the insertion trajectory, which extends vertically in FIG. 1. In the embodiment, the angle of inclination of the rotation axis of the second rotary member 1b is 15 degrees. When the second rotary member 1b is rotated by 180 degrees, the insertion trajectory is inclined by a maximum amount, i.e., at 30 degrees. Rotating the second rotary member 1b gradually changes an orientation of the insertion trajectory as well as an angle of inclination thereof. The needle-like instrument 4 can be guided to the insertion trajectory in any orientation at any angle by rotating the second rotary member 1b in combination with rotation of the first rotary member 1a. As regards a method of obtaining the angle of the first rotary member 1a and that of the second rotary member 1b relative to a puncture target position, a typical inverse kinematics calculation can be used. A detailed description thereof is omitted.

Needle Sensor

An exemplary configuration of the needle sensor 52 in the embodiment will now be described with reference to FIG. 2.

The configuration illustrated in FIG. 2 includes a push switch. FIG. 2 is a schematic cross-sectional view of the guide unit 5 in FIG. 1. The guide unit 5 includes a push switch 53 such that a pressing portion of the push switch 53 is exposed in the needle attachment portion 51 as illustrated in FIG. 2. When the needle is attached to the needle attachment portion 51, the push switch 53 is pressed and turned on. Thus, a detection signal indicative of attachment of the needle-like instrument 4 can be obtained.

System Configuration

Figure 3:
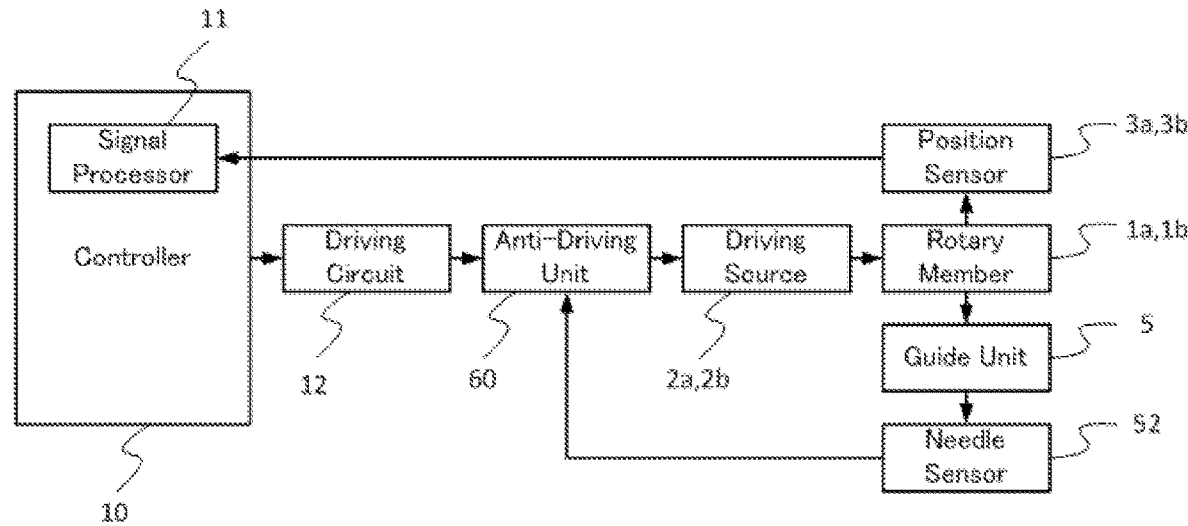
FIG. 3 illustrates an exemplary system configuration in the first embodiment.

An exemplary system configuration in the embodiment will now be described with reference to FIG. 3.

The first driving source 2a and the second driving source 2b are connected to a controller 10 by a driving circuit 12 and an anti-driving unit 60.

The controller 10 allows a signal processor 11 to process positional information obtained by the two position sensors 3a and 3b, and controls the two driving sources 2a and 2b in accordance with the information. The driving circuit 12 outputs a driving signal in accordance with an instruction from the controller 10. The two driving sources 2a and 2b are driven in accordance with the driving signal, thus rotating the first rotary member 1a and the second rotary member 1b.

Anti-Driving Unit

In the embodiment, the anti-driving unit 60 includes an interrupting circuit capable of interrupting the driving signal output from the driving circuit 12. The anti-driving unit 60 interrupts the driving signal in response to a detection signal from the needle sensor 52. For example, the interrupting circuit can be achieved by, for example, a relay or a semiconductor device (e.g., a metal-oxide semiconductor field-effect transistor, or MOS FET).

The anti-driving unit 60, including the interrupting circuit, does not necessarily have to be disposed on an output signal line of the driving circuit 12. For example, the anti-driving unit 60 may be interposed between the controller 10 and the driving circuit 12 to prevent an instruction from being transmitted from the controller 10 to the driving circuit 12. In such a configuration, actuation of the anti-driving unit 60 stops the driving circuit 12 from outputting a signal in a manner similar to the above-described configuration, thus preventing driving of the two driving sources 2a and 2b.

Operation

In the above-described configuration, when the needle-like instrument 4 is attached to the needle attachment portion 51 of the guide unit 5, the push switch 53 of the needle sensor 52 is pressed, so that attachment of the needle is detected. The anti-driving unit 60, including the interrupting circuit, interrupts a driving signal output from the driving circuit 12 in response to a detection signal from the needle sensor 52. Consequently, if a driving instruction is accidentally transmitted from the controller 10 to the driving circuit 12, any driving signal would not be input to the two driving sources 2a and 2b and the two driving sources 2a and 2b would not accordingly be driven.

Modifications

Variety of Needle Sensors

Although the needle sensor 52 including the push switch 53 has been described in the embodiment, the needle sensor 52 may have any configuration capable of detecting attachment of the needle-like instrument 4 to the needle attachment portion 51.

Figures 4A, 4B, 4C, 4D:
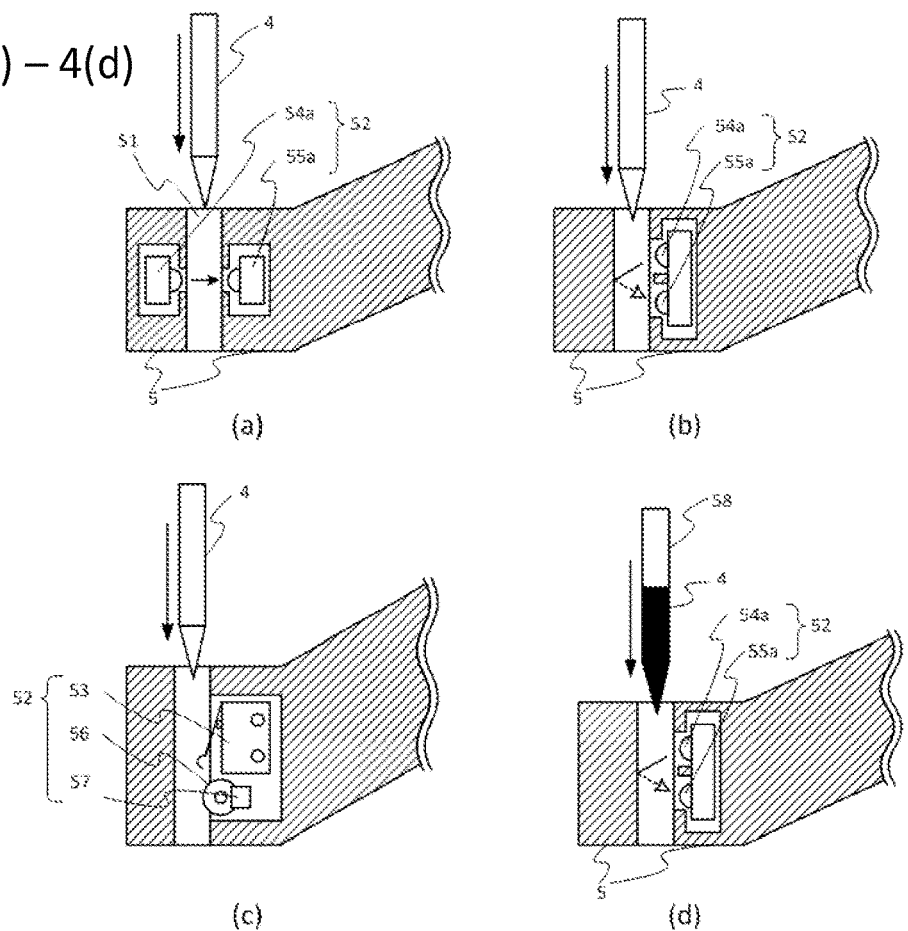
FIGS. 4(a) to 4(d) illustrate modifications of the needle sensor in the first embodiment.

For example, the needle sensor 52 may be a photo-interrupter including a light emitting element 54a and a light receiving element 55a as illustrated in FIG. 4(a). In such a configuration, while the needle-like instrument 4 is not attached to the needle attachment portion 51, light emitted from the light emitting element 54a enters the light receiving element 55a. When the needle-like instrument 4 is attached to the needle attachment portion 51, light emitted from the light emitting element 54a is interrupted by the needle-like instrument 4, and thus inhibited from entering the light receiving element 55a. The light receiving element 55a detects such a change, thus detecting attachment of the needle-like instrument 4.

The needle sensor 52 may be a photo-reflector including a light emitting element 54b and a light receiving element 55b as illustrated in FIG. 4(b). In such a configuration, an inner wall of the needle attachment portion 51 may be processed so as to have a non-reflective surface. While the needle-like instrument 4 is not attached to the needle attachment portion 51, light emitted from the light emitting element 54b is not reflected and accordingly does not enter the light receiving element 55b. When the needle-like instrument 4 is attached to the needle attachment portion 51, light emitted from the light emitting element 54b is reflected by the surface of the needle-like instrument 4, so that the light enters the light receiving element 55b. The light receiving element 55b detects such a change, thus detecting attachment of the needle-like instrument 4.

Detection of Distance of Movement

Although the needle sensor 52 for detecting attachment of the needle-like instrument 4 has been described in the embodiment, the needle sensor 52 may have any other configuration. For example, if the guide unit 5 is disposed at a distance from a surface of a puncture target as in the embodiment, the needle sensor 52 may be configured to enable the needle-like instrument 4 to move in the insertion trajectory to such an extent that the needle-like instrument 4 does not reach the puncture target.

For example, as illustrated in FIG. 4(c), the needle sensor 52 may include the push switch 53, a roller 56 rotating in response to movement of the needle-like instrument 4, and a rotation sensor 57 that detects an amount of rotation of the roller 56. In such a configuration of FIG. 4(c), when the needle-like instrument 4 is attached to the needle attachment portion 51, the push switch 53 is first pressed, thus detecting attachment of the needle-like instrument 4. In this state, further movement of the needle-like instrument 4 in the insertion trajectory allows the needle-like instrument 4 to come into contact with the roller 56 protruding from the inner wall of the needle attachment portion 51. As the needle-like instrument 4 is moved in the insertion trajectory, the roller 56 rotates in response to movement. The rotation sensor 57 detects the amount of rotation, thus detecting a distance of movement of the needle-like instrument 4. For example, assuming that the guide unit 5 is located at a distance of 50 mm from the surface of the puncture target, the needle sensor 52 may be set so as to detect a distance exceeding 45 mm so that the anti-driving unit 60 can be actuated before the needle-like instrument 4 comes into contact with the puncture target.

According to a modification of the configuration including the photo-reflector, as illustrated in FIG. 4(d), a distal portion of the needle-like instrument 4 may be processed so as to have a non-reflective surface 58 so that the needle-like instrument 4 can be detected only in response to insertion of a reflective surface of the needle-like instrument 4. For example, the non-reflective surface 58 may extend 45 mm from a distal tip of the needle-like instrument 4. The needle-like instrument 4 can be detected only when the needle-like instrument 4 is inserted into the needle attachment portion 51 by 45 mm or more. In other embodiments, the non-reflective surface 58 may extend shorter or longer distances from distal tip of the needle-like instrument 4 to optimize the position at which the needle-like instrument 4 is detected for a specific embodiment.

The needle sensor 52 may include an image sensor for measuring the surface of the needle-like instrument 4 to detect the distance of movement of the needle-like instrument 4.

In some embodiments, the arrangement of the reflective surface and the non-reflective surface may be reversed from the arrangement shown in FIGS. 4(b) and 4(d).

Detachment of Guide Unit

Figures 5, 5A:
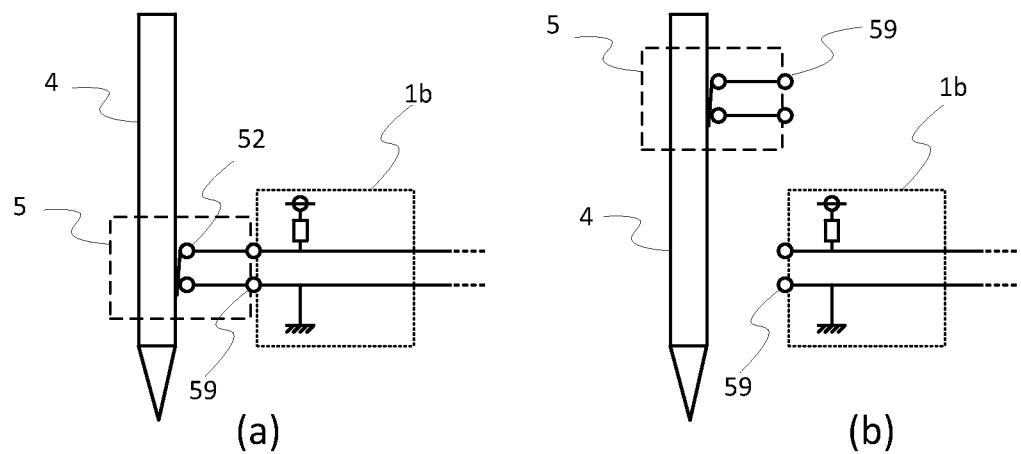

According to another modification, the guide unit 5 may be detachable from the second rotary member 1b. In such a configuration, as illustrated in FIG. 5(a), a detachment sensor 59 for detecting detachment of the guide unit 15 is provided for a connection portion of the guide unit 5. For example, a circuit can be configured such that a connector is connected to a needle detection signal line and pull-up is achieved by the second rotary member 1b. While the guide unit 5 and the needle sensor 52 included in the guide unit 5 are detached as illustrated in FIG. 5B, a signal identical to a signal indicative of non-detection of the needle by the needle sensor 52 can be output. For example, to insert a plurality of needle-like instruments 4 into the puncture target, the guide unit 5 may be detached upon insertion of a first needle-like instrument 4. Consequently, the two rotary members 1a and 1b can be driven to a guide position for insertion of a second needle-like instrument 4.

The detachment sensor 59 may have a configuration different from the one described above having the connector connected to the needle detection signal line. An individual switch for detecting detachment may be provided and connected to provide an input signal to suspend a function of the anti-driving unit 60.

Variety of Anti-Driving Units

Although the anti-driving unit 60 including the interrupting circuit for interrupting a driving signal has been described in the embodiment, the anti-driving unit 60 is not limited to the interrupting circuit. For example, the anti-driving unit 60 may be achieved using any method, for example, a method of suspending power supply to the driving circuit 12. Alternatively, the driving circuit 12 may be allowed to have an operation stop function and an operation of the driving circuit 12 may be stopped using this function. Furthermore, the anti-driving unit 60 may be achieved as a command to stop the controller 10 from generating or outputting an instruction signal to the driving circuit 12.

In addition, the anti-driving unit 60 may be any mechanism that prevents the first rotary member 1a from being driven relative to the base 7 and prevents the second rotary member 1b from being driven relative to the first rotary member 1a. For example, the anti-driving unit 60 may include a brake. In such a configuration, the brake can be actuated upon detection of the needle-like instrument 4 by the needle sensor 52. Consequently, if the driving circuit 12 outputs a driving signal to the driving sources 2a and 2b, the rotary members 1a and 1b are prevented from being driven while the brake is operating.

The anti-driving unit 60 may be a clutch mechanism that transmits or interrupts a driving force from the driving sources to the rotary members. In such a configuration, while the needle-like instrument 4 is not attached to the needle attachment portion 51, a clutch is engaged to transmit the driving force, thus driving the rotary members 1a and 1b. On the other hand, when the needle-like instrument 4 is attached to the needle attachment portion 51, the clutch is disengaged in response to a detection signal indicative of attachment. Consequently, transmission of the driving force is interrupted. Any of the above-described configurations of the anti-driving unit 60 prevents the rotary members 1a and 1b from being driven during attachment of the needle-like instrument 4 if the driving circuit 12 outputs a driving signal to the driving sources 2a and 2b. In the case where the anti-driving unit 60 is the clutch mechanism, the rotary members 1a and 1b can be moved manually while the clutch is disengaged to interrupt driving force transmission. Thus, the rotary members 1a and 1b can be moved manually by an operator or can be moved in a direction in which stress applied from a human body is relieved.

Although the anti-driving unit 60 is actuated directly in response to a detection signal from the needle sensor 52 in the embodiment, the anti-driving unit 60 may be actuated in another manner. For example, the controller 10 may actuate the anti-driving unit 60 in response to receiving a detection signal.

Variety of Mechanisms

Figure 6:
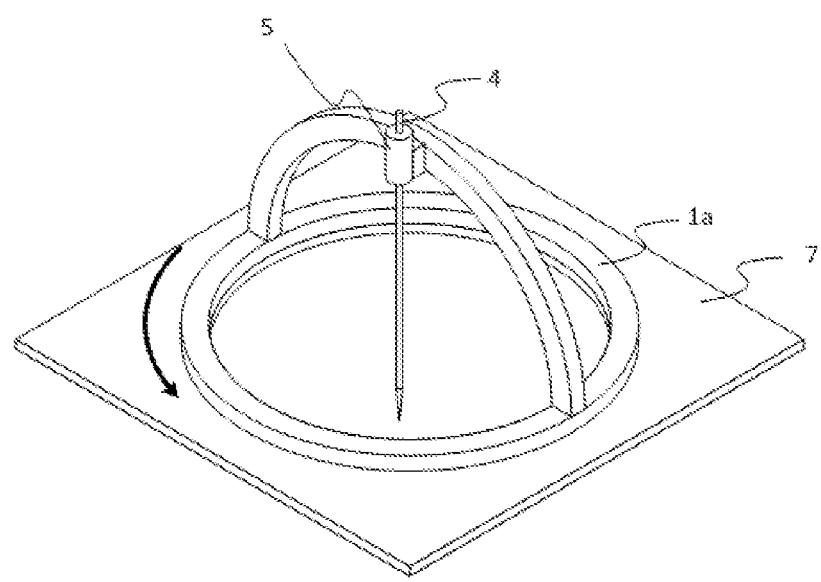
FIG. 6 illustrates a mechanism (including a ring-shaped member and an arcuate member) in accordance with a modification.

Although the mechanism for guiding the needle-like instrument 4 to the insertion trajectory using the two ring-shaped rotary members 1a and 1b has been described in the embodiment, the mechanism may have any configuration. For example, the mechanism may include two arcuate rotary members as described in U.S. Patent Application Publication No. 2006/0229641. Alternatively, as illustrated in FIG. 6, the mechanism may include an arcuate member disposed on the ring-shaped rotary member 1a and may be configured such that the guide unit 5 is movable on the arcuate member.

Figure 7A:
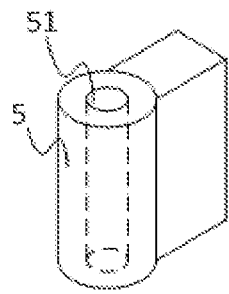
FIGS. 7(a) and 7(b) illustrates a needle attachment portion in accordance with a modification of the first embodiment.
Figure 7B:
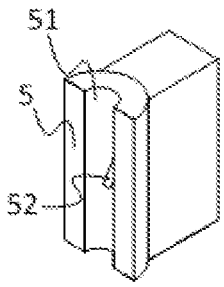

Although the hole-shaped needle attachment portion 51 has been described in the embodiment, in other embodiments, the needle attachment portion 51 may be a groove as illustrated in FIGS. 7(a) and 7(b). Such a configuration also allows the needle sensor 52, described in the embodiment, to detect attachment of the needle-like instrument 4.

Second Embodiment

Figure 8:
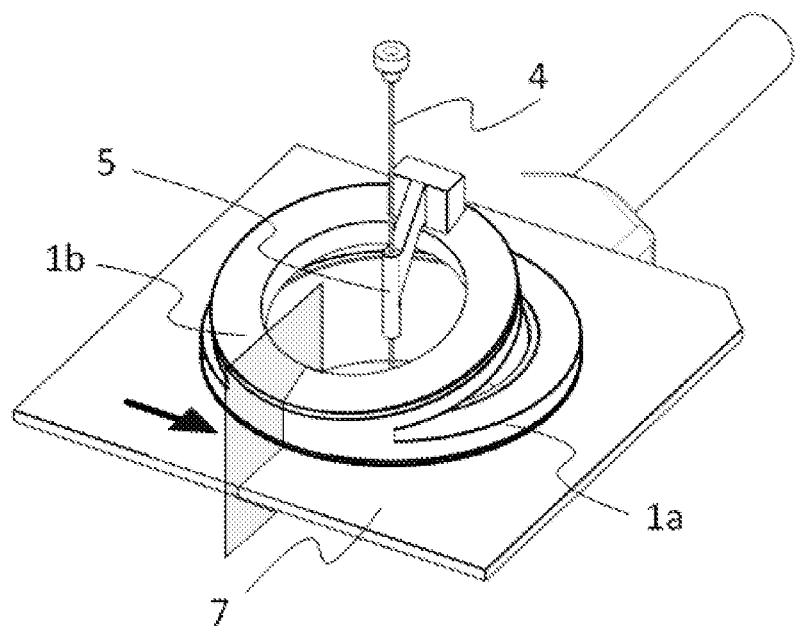
FIG. 8 illustrates an exemplary configuration of a mechanism in a second embodiment.

A second embodiment will be described with reference to FIGS. 8 and 9. A medical assist device according to the second embodiment includes vibration-type actuators. A needle-like instrument guiding mechanism of the medical assist device according to the second embodiment and changing the insertion trajectory of a needle-like instrument 4 are the same as those in the first embodiment. The second embodiment differs from the first embodiment in that the vibration-type actuators are used as driving sources. A configuration for incorporating the vibration-type actuators into the medical assist device will be described and an anti-driving unit 60 in the use of the vibration-type actuators will then be described.

Configuration of Vibration-Type Actuator

An exemplary configuration of the mechanism in the second embodiment will now be described with reference to FIG. 9. FIG. 9 is a cross-sectional view of the mechanism as viewed in a direction of arrow in FIG. 8.

A first driving source 2a is disposed between a base 7 and a first rotary member 1a and the first rotary member 1a is driven by the first driving source 2a in a manner similar to the first embodiment. Specifically, the first driving source 2a is a ring-shaped vibration-type actuator that includes a pressurizing unit 20a, a piezoelectric element 21a, a vibrating member 22a, and a moving member 23a as illustrated in FIG. 9. The piezoelectric element 21a is excited to vibrate in response to an input electrical signal. The vibrating member 22a amplifies vibration of the excited piezoelectric element 21a to produce flexural vibration. The pressurizing unit 20a applies pressure to the vibrating member 22a and the moving member 23a. The vibration of the vibrating member 22a is transmitted to the moving member 23a by friction, so that the vibrating member 22a and the moving member 23a are rotated relative to each other. In the present embodiment, the pressurizing unit 20a, the piezoelectric element 21a, and the vibrating member 22a are provided for the first rotary member 1a, and the moving member 23a is fixed to the base 7. Consequently, the first rotary member 1a is rotated about a rotation axis perpendicular to the base 7 by the first driving source 2a.

A second rotary member 1b is disposed on the first rotary member 1a such that the second rotary member 1b has a rotation axis at a predetermined angle to the rotation axis of the first rotary member 1a. In this embodiment, the rotation axis of the second rotary member 1b is inclined at 15 degrees.

Figure 9:
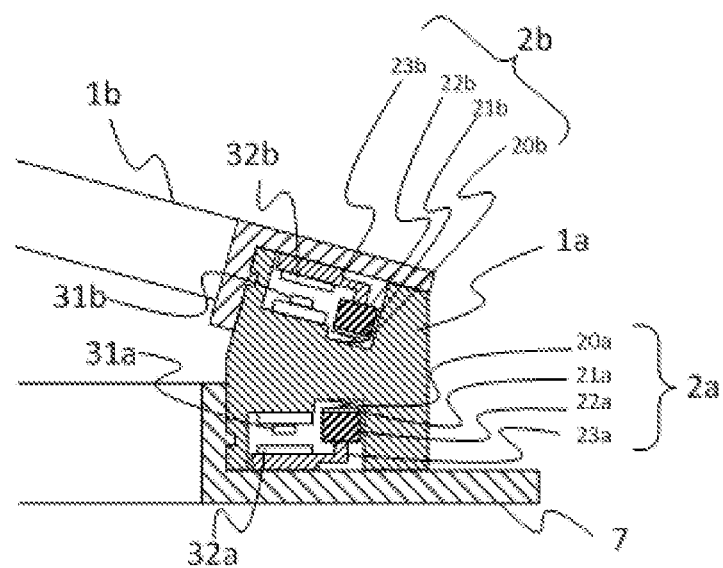
FIG. 9 is a cross-sectional view of the mechanism in the second embodiment.

Referring to FIG. 9, a second driving source 2b is disposed between the first rotary member 1a and the second rotary member 1b. Like the first driving source 2a, the second driving source 2b includes a pressurizing unit 20b, a piezoelectric element 21b, a vibrating member 22b, and a moving member 23b. The second rotary member 1b is driven by the second driving source 2b.

Principle of Driving of Vibration-Type Actuator

Each driving source in the embodiment will now be described in detail. The vibrating member 22 includes a ring-shaped elastic body and a plurality of protrusions 24 arranged at predetermined circumferential positions. The protrusions 24 excite a wave circumferentially traveling in the ring-shaped vibrating member 22. Two-phase alternating current (AC) voltages out of phase are applied to the piezoelectric element 21, serving as two groups of electromechanical energy transducer elements out of positional phase, bonded to and disposed on a first surface of the vibrating member 22, thus exciting the vibrating member 22 in a traveling wave mode. This causes elliptic motion of the protrusions 24 of the vibrating member 22. The pressurizing unit 20 allows the protrusions 24 to be in pressure contact with the moving member 23. The elliptic motion of the protrusions 24 produces circumferential friction. Consequently, the moving member 23 is driven relative to the vibrating member 22.

Reversing the direction of a phase difference between the two-phase AC voltages applied to the two groups of the piezoelectric element 21 reverses the direction of the traveling wave and that of the elliptic motion, thus reversing rotation of the moving member 23. A phase difference of 0 or 180 degrees causes no wave traveling in the vibrating member 22 but produces standing wave vibration, which applies no rotational driving force to the moving member 23.

Anti-Driving Unit for Vibration-Type Actuator

In the configuration including the driving sources 2a and 2b driven by the above-described two-phase AC voltages, the anti-driving unit 60 interrupts only one phase of the two-phase AC voltages. Consequently, the vibrating members 22 fail to actively produce traveling wave vibration. If a driving circuit 12 outputs driving signals, therefore, the driving sources 2a and 2b fail to achieve rotational driving.

On the other hand, the driving signal of the other phase is applied to the piezoelectric elements 21, thus exciting standing wave vibration in the vibrating members 22. Usually, the vibrating members 22 and the moving members 23 are pressurized to produce friction by the pressurizing units 20, thus providing high holding torque. Accordingly, it is difficult to manually drive the rotary members 1a and 1b. However, standing wave vibration of the vibrating members 22 reduces the area of contact between each vibrating member 22 and the corresponding moving member 23 and the time of contact there between, thus making friction torque less than normal holding torque. Consequently, the rotary members 1a and 1b can be readily driven manually.

According to the embodiment, while the needle-like instrument 4 is attached to the medical assist device including the vibration-type actuators, the two rotary members 1a and 1b are not actively driven. In this state, holding torque unique to the vibration-type actuators can be reduced by applying a one-phase driving signal to the driving sources 2a and 2b. Thus, the operator can operate the rotary members 1a and 1b manually.

Any method other than the method of interrupting a driving signal of one phase of two-phase driving signals may be used. Driving signals in phase may be supplied to both the two groups of the piezoelectric element 21. For example, connection of driving signals output from the driving circuit 12 can be switched by a switch, thus distributing a driving signal of one phase of the two-phase driving signals to the two groups of the piezoelectric element 21. Alternatively, one of two-phase instruction signals input to the driving circuit 12 may be distributed so that the driving circuit 12 outputs driving signals in phase. In such a configuration, the logic of one of the distributed signals can be inverted to produce driving signals in opposite phase to each other. In these configurations, the switch for switching between connections serves as the anti-driving unit 60. Furthermore, a detection signal output from a needle sensor 52 may be input to a controller 10 and the controller 10 may instruct the driving circuit 12 to output two-phase driving signals to be in phase with or in opposite phase to each other.

Release of Applied Pressure

Although the anti-driving unit 60 for the vibration-type actuators has been described as a component configured to interrupt a driving signal of one phase of two-phase driving signals, the anti-driving unit 60 may have any other configuration. For example, each pressurizing unit 20 includes a spring in the embodiment. The pressurizing unit 20 may be a mechanism capable of changing applied pressure, for example, an air cylinder. In such a configuration, if applied pressure is reduced, friction would inadequately act between the vibrating member 22 and the moving member 23. If the vibrating member 22 vibrates in the traveling wave mode, the moving member 23 would not be driven by such vibration. Additionally, no friction between the vibrating member 22 and the moving member 23 leads to reduced holding torque. The rotary members 1a and 1b can be driven manually.

Supplementary Explanation

Although the needle sensor 52 has not been described in detail in the embodiment, any of the needle sensors 52 described in the first embodiment and the modifications thereof and a needle sensor 52 which will be described in a third embodiment may be used. In the use of the vibration-type actuators, the configuration is not limited to that in the embodiment. The anti-driving unit 60 in the first embodiment may be used in the configuration including the vibration-type actuators.

Types of Vibration-Type Actuator

Although the ring-shaped vibration-type actuators have been described in the second embodiment, the actuators may be any type in which the vibrating member and the moving member are driven by friction. For example, the vibration-type actuator described in U.S. Pat. No. 7,187,104, No. 8-237971, or No. 5-083961 may be used. Alternatively, any other vibration-type actuator may be used. Driving methods will now be described with respect to a case where the vibration-type actuator described in U.S. Pat. No. 7,187,104 is included in the configuration in the second embodiment, a case where the vibration-type actuator described in Japanese Patent Laid-Open No. 8-237971 is included in the configuration in the second embodiment, and a case where the vibration-type actuator described in Japanese Patent Laid-Open No. 5-083961 is included in the configuration in the second embodiment.

Figures 11A, 11B, 11C, 11D:
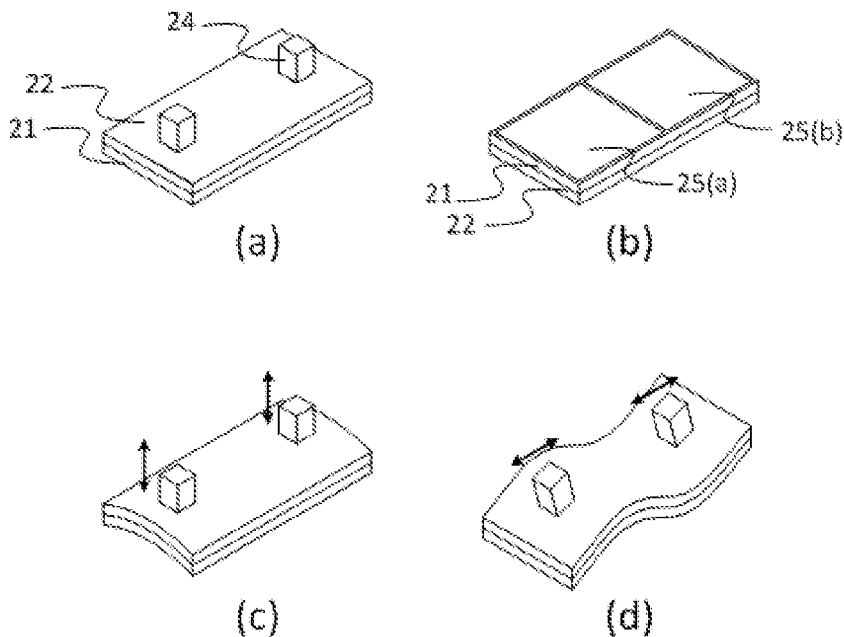
FIGS. 11(a) to 11(d) illustrate motions of a vibration-type actuator described in U.S. Pat. No. 7,187,104.

FIGS. 11(a) to 11(d) are diagrams illustrating an operation of the vibration-type actuator described in U.S. Pat. No. 7,187,104. FIGS. 11(a) and 11(b) illustrate an exemplary configuration of this vibration-type actuator and arrangement of electrodes. FIG. 11(c) illustrates vibration of a vibrating member 22 in which AC voltages in phase are applied to two electrodes 25(a) and 25(b), and illustrates protrusions 24 vibrating longitudinally (or upward and downward). FIG. 11(d) illustrates vibration of the vibrating member 22 in which AC voltages in opposite phase are applied to the two electrodes 25(a) and 25(b), and illustrates the protrusions 24 vibrating laterally (or transversely). Typically, AC voltages having a predetermined phase difference therebetween are applied to the electrodes 25(a) and 25(b), thus causing longitudinal vibration and lateral vibration each having a phase varying with time, leading to elliptic motion of the protrusions 24. The elliptic motion causes the moving member 23 to be driven.

Figures 12A, 12B, 12C:
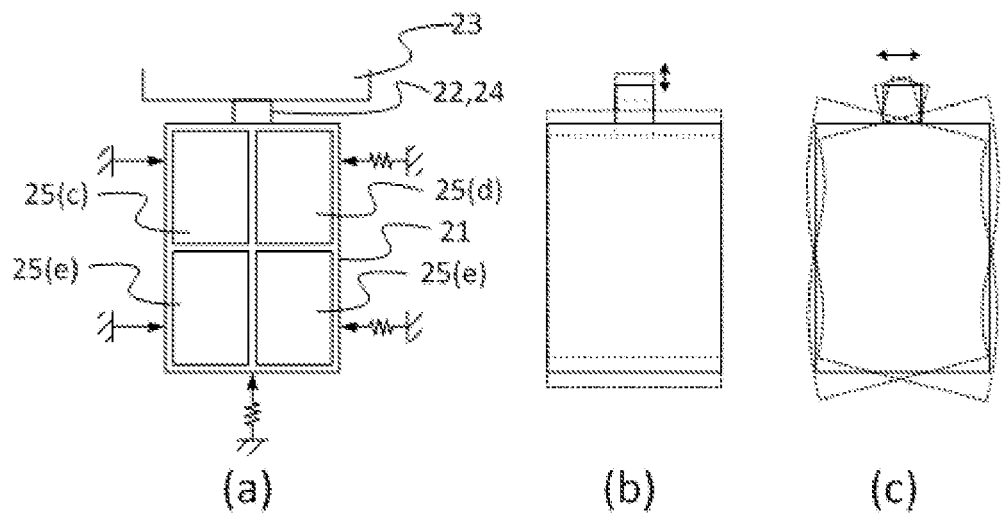
FIGS. 12(a) to 12(c) illustrate motions of a vibration-type actuator described in Japanese Patent Laid-Open No. 8-237971.

FIGS. 12(a) to 12(c) are diagrams illustrating an operation of the vibration-type actuator described in Japanese Patent Laid-Open No. 8-237971. FIG. 12(a) illustrates an exemplary configuration of the vibration-type actuator and arrangement of four electrodes 25(c), 25(d), 25(e), and 25(f). The electrodes 25(c) and 25(f) are connected by a wire such that the electrodes are supplied with the same driving signal. The electrodes 25(d) and 25(e) are similarly connected by a wire. FIG. 12(b) illustrates vibration of a vibrating member 22 upon application of AC voltages in phase to the two pairs of electrodes, and illustrates a protrusion 24 vibrating longitudinally (or upward and downward). FIG. 12(c) illustrates vibration of the vibrating member 22 upon application of AC voltages in opposite phase to the two pairs of electrodes, and illustrates the protrusion 24 vibrating laterally (or transversely). Typically, AC voltages having a predetermined phase difference therebetween are applied to the two pairs of electrodes in a manner similar to U.S. Pat. No. 7,187,104, thus causing longitudinal vibration and lateral vibration each having a phase varying with time, leading to elliptic motion of the protrusion 24. The elliptic motion causes the moving member 23 to be driven.

In the case where the vibration-type actuator described in U.S. Pat. No. 7,187,104 or Laid Open Japanese Application No. 8-237971 is included in the configuration in the second embodiment, the anti-driving unit 60 switches between driving signals and supplies the driving signals in phase to the piezoelectric element. Consequently, a driving force produced by the vibration-type actuator described in U.S. Pat. No. 7,187,104 or Laid Open Japanese Application No. 8-237971 can be interrupted. Furthermore, the time of contact between the vibrating member 22 and the moving member 23 is reduced, thus reducing holding torque.

On the other hand, when the anti-driving unit 60 supplies driving signals in opposite phase, lateral vibration is caused as an operation observed within a restricted period of time. Since the lateral vibration is reciprocating vibration, the moving member 23 is not driven from a macroscopic viewpoint. Accordingly, the anti-driving unit 60 achieves its function when supplying driving signals in opposite phase. In this case, the time of contact between the vibrating member 22 and the moving member 23 is not reduced. The vibrating member 22, however, is in vibrating contact with the moving member 23 and friction between the vibrating member 22 and the moving member 23 is in a dynamical friction state, which results in holding torque lower than that in a static friction state in which no vibration is caused.

In the use of each of these vibration-type actuators, the anti-driving unit 60, configured to supply either driving signals in phase or driving signals in opposite phase, achieves its function because any driving force is not generated in response to either of the driving signals in phase and the driving signals in opposite phase as described above.

The anti-driving unit 60 can supply driving signals to excite only longitudinal vibration in terms of no vibrations in a driving direction observed microscopically and in terms of a reduction in holding torque.

The vibration-type actuator described in Japanese Patent Laid-Open No. 5-083961 will now be described. The vibration-type actuator in Japanese Patent Laid-Open No. 5-083961 operates in such a manner that a piezoelectric element for generating torsional vibration and a piezoelectric element for generating longitudinal vibration to control contact between a vibrating member 22 and a moving member 23 are used in combination to generate a driving force. In the case where this actuator is included in the configuration in the second embodiment, the anti-driving unit 60 can interrupt a driving signal supplied to the piezoelectric element for generating torsional vibration, thus interrupting a driving force. Furthermore, the anti-driving unit 60 may interrupt a driving signal supplied to the piezoelectric element for generating longitudinal vibration for the following reason: under only torsional vibration, the moving member 23 tends to vibrate in the driving direction from a microscopic viewpoint but is stopped from being driven from a macroscopic viewpoint.

The above-described driving of the vibration-type actuator described in Japanese Patent Laid-Open No. 5-083961 allows a reduction in holding torque and manual operation in a manner similar to the cases using the vibration-type actuators described in U.S. Pat. No. 7,187,104 and Laid Open Japanese Application No. 8-237971.

Although the piezoelectric element is used as an electromechanical energy transducer of the vibration-type actuator in the second embodiment, the transducer is not limited to the piezoelectric element. For example, an electrostriction element or a magnetostriction element may be used.

Third Embodiment

Figure 10:
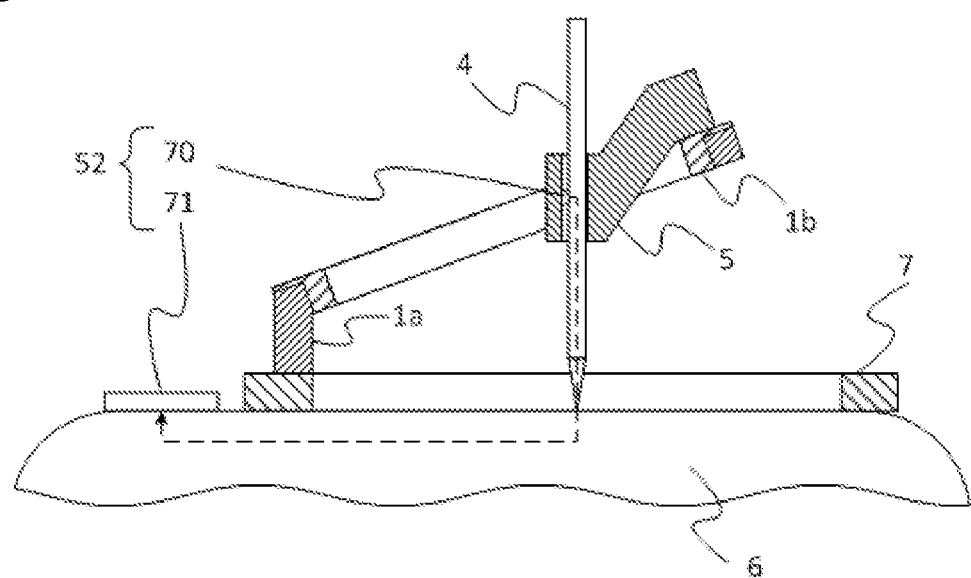
FIG. 10 illustrates an exemplary configuration of a needle sensor in a third embodiment.

A third embodiment will be described with reference to FIG. 10. Each of a needle-like instrument guiding mechanism of a medical assist device according to the third embodiment, changing the insertion trajectory of a needle-like instrument, and an anti-driving unit 60 of the device may be any of those described in the first and second embodiments.

As a feature of the third embodiment, a needle sensor 52 will now be described with reference to FIG. 10.

The needle sensor 52 in the present embodiment includes a signal output unit 70 and a signal detecting unit 71. The signal output unit 70 applies an output signal to a conductive needle-like instrument 4 through an electrode disposed in a needle attachment portion 51. The signal detecting unit 71 is disposed on a body surface to detect a change in potential at the body surface.

In such a configuration, while the needle-like instrument 4 is not in contact with a puncture target 6, the signal detecting unit 71 fails to detect a signal output from the signal output unit 70. When the needle-like instrument 4 comes into contact with and is inserted into the puncture target 6, the puncture target 6 is included in a signal transmission path. Consequently, a signal output from the signal output unit 70 travels through the body surface of the puncture target 6 and is then detected by the signal detecting unit 71. The anti-driving unit 60 is actuated in response to the detected signal, thereby preventing driving of two rotary members only while the needle-like instrument 4 is in contact with the puncture target 6.

Although an output signal from the signal output unit 70 is applied to the needle-like instrument 4 through the signal output unit 70 disposed in the needle attachment portion 51 in this embodiment, the signal may be applied in another way. For example, the signal may be applied independently of a guide unit 5, for example, through a wire.

It is only required that the signal detecting unit 71 measures a potential at the body surface of the puncture target 6. For example, the signal detecting unit 71 may include an electrode disposed on a bottom surface of a base 7 to contact the body surface of the puncture target 6.

Although a signal is applied to the needle-like instrument 4 and is detected from the body surface in the embodiment, the application and detection of the signal may be inverted such that the signal is applied to the body surface and is detected through the needle-like instrument 4.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

What is claimed is:

1. A medical assist device comprising:
   a guide unit configured to guide a needle-like instrument along an insertion trajectory;
   a ring-shaped moving mechanism including the guide unit and configured to be mounted on a body surface of a patient;
   a driving source configured to rotate the ring-shaped moving mechanism around a rotational axis thereof to control the insertion trajectory of the needle-like instrument by changing a position and orientation of the guide unit with respect to the patient;
   a needle sensor configured to detect the needle-like instrument disposed in the guide unit and configured to output a detection signal in response to detecting that the needle-like instrument is disposed in the guide unit; and
   an anti-driving unit configured to, in response to the detection signal from the needle sensor, prevent the driving source from rotating the ring-shaped moving mechanism,
   wherein the anti-driving unit is configured to prevent the ring-shaped moving mechanism from changing the position and orientation of the guide unit in response to the detection signal from the needle sensor,
   wherein the anti-driving unit prevents rotation of the ring-shaped moving mechanism only when the needle-like instrument is in contact with or inserted into the body surface of the patient and the ring-shaped moving mechanism including the guide unit are mounted on the body surface of the patient, and
   wherein the needle sensor includes a detecting unit configured to detect attachment of the needle-like instrument to the guide unit and a distance detecting unit configured to detect a distance of movement of the needle-like instrument relative to the guide unit as the needle-like instrument is guided by the guide unit along the insertion trajectory.

2. The device according to claim 1, wherein the needle sensor detects attachment of the needle-like instrument to the guide unit.

3. The device according to claim 1,
   wherein the needle sensor includes a push switch, and
   wherein the push switch is actuated when the needle-like instrument is attached to the guide unit, and the needle sensor detects the attachment of the needle-like instrument to the guide unit when the push switch is pressed.

4. The device according to claim 1,
wherein the needle sensor includes a light emitting element and a light receiving element,
wherein the light emitting element and the light receiving element are positioned in such a manner that while the needle-like instrument is not attached to the guide unit, the light receiving element receives light emitted from the light emitting element, and while the needle-like instrument is attached to the guide unit, the light emitted from the light emitting element is interrupted, and
wherein the light receiving element outputs the detection signal when the light emitted from the light emitting element is interrupted.

5. The device according to claim 1,
wherein the needle sensor includes a light emitting element and a light receiving element,
wherein the light emitting element and the light receiving element are positioned in such a manner that while the needle-like instrument is not attached to the guide unit, the light receiving element fails to receive light emitted from the light emitting element, and while the needle-like instrument is attached to the guide unit, the needle-like instrument reflects the light emitted from the light emitting element and the reflected light is detected by the light receiving element, and
wherein the light receiving element outputs the detection signal while the light receiving element detects the reflected light.

6. The device according to claim 1,
wherein the distance detecting unit includes
a roller-shaped member configured to rotate in contact with the needle-like instrument, and
a rotation amount detecting section configured to detect an amount of rotation of the roller-shaped member, and
wherein the distance detecting unit detects the distance of movement of the needle-like instrument relative to the guide unit based on the amount of rotation detected by the rotation amount detecting section.

7. The device according to claim 1,
wherein the needle-like instrument has a surface having different reflectivities, and
wherein the distance detecting unit detects movement of the needle-like instrument relative to the guide unit by a predetermined distance based on a change in intensity of reflected light incident on the light receiving element.

8. The device according to claim 1,
wherein the needle sensor includes a signal applying unit configured to apply an electrical signal to the needle-like instrument and a signal detecting unit configured to detect the electrical signal from the body surface of the patient, and
wherein the electrical signal travels through the body surface of the patient and is detected by the signal detecting unit only upon contact and insertion of the needle-like instrument with and into the patient, and the anti-driving unit is actuated in response to the detected signal.

9. The device according to claim 1, wherein, when the anti-driving unit is actuated, the anti-driving unit interrupts a driving instruction or electric power to the driving source.

10. The device according to claim 1,
wherein, when the anti-driving unit is actuated, the anti-driving unit prevents a driving force from being transmitted from the driving source to the ring-shaped moving mechanism.

11. The device according to claim 1,
wherein the anti-driving unit includes a brake mechanism, and
wherein, when the anti-driving unit is actuated, the brake mechanism contacts the ring-shaped moving mechanism or the driving source to prevent driving of the ring-shaped moving mechanism.

12. The device according to claim 1,
wherein the driving source includes a vibration-type actuator that includes an electromechanical energy transducer, a vibrating member configured to be excited to vibrate in response to a driving signal applied to the electromechanical energy transducer, and a moving member having a frictional surface in friction contact with the vibrating member,
wherein the moving member is driven in a predetermined direction by vibration of the excited vibrating member,
wherein the electromechanical energy transducer includes a first electromechanical energy transducer element and a second electromechanical energy transducer element out of positional phase,
wherein a first alternating current voltage as a first driving signal is applied to the first electromechanical energy transducer element to excite the vibrating member to first vibration, and a second alternating current voltage as a second driving signal is applied to the second electromechanical energy transducer element to excite the vibrating member to second vibration, and
wherein the vibration-type actuator drives the moving member by either of the first vibration and the second vibration of the vibrating member or combined vibration of the first and second vibrations.

13. The device according to claim 12, wherein, when the anti-driving unit is actuated, the anti-driving unit interrupts either of the first driving signal and the second driving signal.

14. The device according to claim 12, wherein, when the anti-driving unit is actuated, the anti-driving unit allows either of the first driving signal and the second driving signal to be in phase with or in opposite phase to the other driving signal.

15. The device according to claim 1, further comprising:
a detachment sensor configured to detect detachment of the guide unit from the ring-shaped moving mechanism,
wherein the guide unit is detachable from the ring-shaped moving mechanism, and
wherein the anti-driving unit is stopped from preventing driving in response to a detection signal from the detachment sensor.

16. A medical assist device comprising:
a guide unit configured to guide a needle-like instrument along an insertion trajectory;
a ring-shaped rotary mechanism to which the guide unit is attached, the ring-shaped rotary mechanism configured to be mounted on a body surface of a patient;
a driving source configured to rotate the ring-shaped rotary mechanism around a rotational axis thereof to change a position and posture of the guide unit to thereby change the insertion trajectory of the needle-like instrument;
a needle sensor that is included in the guide unit, that is configured to detect a coupling of the needle-like instrument to the guide unit, and that is configured to output a detection signal in response to detecting the coupling of the needle-like instrument to the guide unit; and an anti-driving unit configured to prevent the driving source from rotating the ring-shaped rotary mechanism in response to receiving the detection signal from the needle sensor, wherein the anti-driving unit is configured to stop the ring-shaped rotary mechanism from changing the position and orientation of the guide unit in response to receiving the detection signal from the needle sensor, wherein the anti-driving unit prevents rotation of the ring-shaped rotary mechanism only when the needle-like instrument is in contact with or inserted into the body surface of the patient and the ring-shaped rotary mechanism to which the guide unit is attached is mounted on the body surface of the patient, and wherein the needle sensor includes one or more of a push switch, a light emitting element, and a light receiving element.

17. The device according to claim 16, wherein the needle sensor is configured to output the detection signal in response to detecting the coupling of the needle-like instrument at a predetermined position relative to the guide unit.

18. The device according to claim 1, wherein the ring-shaped moving mechanism includes a rotary mechanism to which the guide unit is attached.

19. The device according to claim 18, wherein the ring-shaped moving mechanism is mounted on a base.

20. The device according to claim 1,
wherein the ring-shaped moving mechanism includes an arcuate mechanism mounted on the ring-shaped moving mechanism, and
wherein the guide unit is attached to the arcuate mechanism.

21. The device according to claim 1,
wherein the ring-shaped moving mechanism includes first and second ring-shaped rotary members,
wherein the second rotary member has a rotation axis at a predetermined angle with respect to the rotation axis of the first rotary member, and
wherein the guide unit is attached to the second rotary member.

22. The device according to claim 1, wherein the anti-driving unit includes a brake mechanism or a clutch mechanism.

* * * * *